US007351581B2

(12) United States Patent
Aulakh

(10) Patent No.: US 7,351,581 B2
(45) Date of Patent: Apr. 1, 2008

(54) IN VIVO METHOD FOR PRODUCING FEMALE OFFSPRINGS IN BOVINES

(76) Inventor: Balwinder Singh Aulakh, House No. 2234/2C-29, Issanagari, Ludhiana (IN) 141 001

( * ) Notice: Subject to any disclaimer, the term of this patent is extended or adjusted under 35 U.S.C. 154(b) by 611 days.

(21) Appl. No.: 10/450,353

(22) PCT Filed: Dec. 15, 2000

(86) PCT No.: PCT/IN00/00125

§ 371 (c)(1),
(2), (4) Date: Jul. 31, 2003

(87) PCT Pub. No.: WO02/47574

PCT Pub. Date: Jun. 20, 2002

(65) Prior Publication Data

US 2004/0048806 A1 Mar. 11, 2004

(51) Int. Cl.
*C12N 5/00* (2006.01)
*C12P 7/54* (2006.01)

(52) U.S. Cl. ...................... 435/325; 435/140; 424/400; 514/23

(58) Field of Classification Search ................ 435/140, 435/325; 424/400
See application file for complete search history.

(56) References Cited

U.S. PATENT DOCUMENTS 3,219,525 A 11/1965 Berkow
3,749,089 A 7/1973 Derr
4,159,718 A * 7/1979 Bower ........................ 604/212
4,336,801 A 6/1982 Sentell et al.
4,999,283 A 3/1991 Zavos et al.

OTHER PUBLICATIONS

The Vinegar Institute—Frequently Asked Questions at http://www.versatilevinegar.org/faqs.html, 2005.*
To et al., Gender Preselection, J. HOng Kong Med. Assoc., 46(4):331-336 (Dec. 1994).*

* cited by examiner

*Primary Examiner*—Jon Weber
*Assistant Examiner*—Tiffany M. Gough
(74) *Attorney, Agent, or Firm*—Rankin, Hill, Porter & Clark LLP

(57) ABSTRACT

The invention provides an in'vivo method whereby female offsprings can be produced in bovines said method comprising the step of administering a therapeutically effective amount of a material comprising acetic acid, or its pharmaceutically acceptable derivatives to female bovines just after or before insemination.

10 Claims, No Drawings

IN VIVO METHOD FOR PRODUCING FEMALE OFFSPRINGS IN BOVINES

This application is a National Stage application filed under 35 U.S.C 371 of International application PCT/IN00/00125, filed Dec. 15, 2000, which designates the U.S. ,the entire contents of which are hereby incorporated by reference.

TECHNICAL FIELD OF THE INVENTION

The present invention relates to an in vivo method for producing female offsprings in mammals. More specifically, it relates to a novel method for alteration of sex ratio to produce female offsprings, especially in case of bovine and such other animals.

BACKGROUND AND PRIOR ART OF THE INVENTION

Sex determination has been a favorite subject for reproductive physiologists since long. Sex determination is a process whereby the sex of the offspring is decided by sex chromosomes in mammals and by factors such as temperature in certain chordates such as reptiles. Sex assignment and determination in mammals is a method whereby the sex of the offspring is decided even before actual formation of the zygote by the fusion of an ovum with a spermatozoa bearing the sex chromosome of a particular sex and conditions are created such that the combination of chromosomes leading to the formation of a fetus of desired sex. Sex ratio is an indicator/measure devised to ascertain the proportion of males and females in a given population. There have been several attempts in the prior art to alter the sex ratio in mammals.

Some chordate species are known to be temperature dependent for sexual determination (TSD) (Bull, J. J 1980, Qrtly Rev Biol, 53, 3-21, 1980). In case of such animals, the sex of the offspring instead of being determined by sex chromosomes, is determined by the temperature at which egg is incubated. Further, there are certain species where application of certain hormones alters the sex of the offspring. Such species include certain reptiles and ratites. Such attempts to alter the sex are discussed and disclosed in U.S. Pat. Nos. 5,201,280 and 5,377,618.

However, in case of mammals, sex of the offspring is determined by random combinations of X- or Y-chromosome bearing sperms with an ovum always containing the X-chromosome and giving rise to a sex ratio of almost 50:50. In case of mammals also, some workers have tried to manipulate sex ratios. Manipulation of sex ratio gains prominence with the fact that mammals are an important family and success in altering the sex ratio in mammals, especially to the female side, has advantages in milk and meat producing species and in evolving livestock of better quality. This becomes doubly important in cross-breeding programs where 50% of the offsprings turn out to be of female sex and remaining 50% of male sex. The offsprings of the male sex are not generally favoured in the livestock industry. Altering the sex ratio, thereby leading to preferential production of females may make such cross-breeding programs a tremendous success. This also keeps the proportion of male populations of these species to the minimum extent as required for insemination purposes only.

In the light of these advantages, many workers have attempted to alter sex ratios throughout the last century. A number of attempts made about 1940 were based on the assumption that vaginal pH controlled the sex of the offspring. Schroeder V. (Physico-chemical methods of sex regulation of the progeny of mammals. Abstr in J. Hered 1941: 32:248) discussed efficacy of physico-chemical methods to regulate sex ratios. But conclusive evidence of efficacy of these methods was not found in careful scientific investigations (Salisbury and VanDemark: Physiology of reproduction and artificial insemination in cattle, 1961).

Later on, this approach of change in vaginal pH was deserted and reproductive physiologists concentrated on attempts to produce sexed semen. A sexed semen contains either X- or Y- bearing sperms in complete or accentuated concentrations, and which, when combined with ova, containing X-chromosome, either female (XX) or male (XY) offsprings are produced in complete or relatively greater proportions.

Several workers have carried on research on this subject and used different techniques to separate X- and Y- bearing sperms. (The sperms only contain X-Y-chromosomes, however, the applicant has referred the sperms as X- or Y- for convenience.) Lindahl in 1953 reported success in producing sexed semen in bulls (Counter-streaming of bull spermatozoa, Nature: 1956, 178: 491-92). Gordon M. J. (Scientific American, 199: 87-94, 1958) also discussed a method to control the sex ratio. This study represented yet another approach to produce sexed semen. Bhattacharaya et al (An Attempt to determine the sex ratio of calves by artificial insemination with spermatozoa separated by sedimentation, Nature 211: 863: 1966), were able to achieve a degree of success in producing sexed semen in bulls. Ericsson (Isolation of fractions rich in human Y-sperm, Nature 1973: 246:421) reported a method to get fractions richer in human Y-sperms. Gledhill (Control of mammalian sex by sexing the sperm: Fertil. Steril. 1983, 40(5): 572-74) and Corson et al ("Sex selection by sperm separation and insemination", Fertil. Steril, 1984: 42:756) also reported new methods to produce sexed semen. However, no predictable and repeatable methodology could be evolved by these workers resulting in significant shift in sex ratio (Hunter, Reproduction of Farm Animals, 1982, 138-139), has also stated that despite all these attempts, modification of sex ratio still remains a mirage on the horizon. The reason behind this may be that sperms are haploid cells and haploid cells as distinct from diploid cells express a change in genetic constitution in surface characteristics, is still not clear (Hunter, 1982). Also, as pointed by Hafez (Reproduction in Farm Animals, fifth edition, 1987, 499), these attempts were hampered by the lack of laboratory tests to evaluate the degree of sperm separation.

Sex determination was reported also on a different line. Certain compounds, hormones, sera etc. were reported to have an effect on the altering of sex ratio. Bennett & Boyce, (Sex ratio in progeny of mice inseminated with sperm treated with HY antiserum, Nature, 246:308, 1973) reported that insemination with sperm treated with antisera to a Y-linked histocompatibility antigen produced 45.4% males compared with 53.4% for controls in mice. Barrat and Leger (J. Gyneiol. Obstet. Biol. Reprod, Paris, 8, 332, 1979) reported that administration of clomiphene citrate and/or gonadotropins resulted in 8.7% lowering of sex ratio. Beernik et al ("Factors influencing human sex ratio," presented at the Annual meeting of American Fertility Society, 1984) reported similar results for humans. Sampson et al ("Gender After induction of Ovulation and artificial insemination" : Fertil. Steril. 40; pg 481, 1983) reported that with the induction of super ovulation, multiple births showed a marked skewness towards male births. Mitra & Chowdhary (Abstr in animal Breed, 58(4): No.2354, 1990) showed that glyceryl phosphorus choline diesterase activity of uterine fluid had an effect in altering the secondary sex ratio (i.e. at birth) in rats.

Thus, the prior art is replete with attempts to control the sex of mammalian offspring because the outcome of this research is valuable in a variety of economic conditions, for example, preferential birth of female calves in dairy herds would improve the rate of achieving superior animal strains by selective breeding. It would also be valuable medically where for example it is desired to prevent the birth of sons to mothers who are carriers of a genetic diseases which affect only males.

Each of the above attempts in the prior art represent different approaches towards sex assignment or production of off-springs of a desired sex. Recognizing the need to develop a simple and easy method for the assignment of sex or production of offsprings of significant number of females, the applicants conducted a thorough investigation on various chemicals capable of sex assignment and determination in offsprings. With the singular objective of increasing female population in livestock, the applicants screened a few chemicals and to their surprise found that a material essentially containing an acetyl group, such as vinegar, could be successfully used to achieve the above purpose. In addition, the applicant has arrived at a methodology to obtain female population, which is very cost-effective, easy to perform and does not involve in vitro treatment of sperms.

OBJECTS OF THE INVENTION

The main objective of the invention is to provide an in vivo method whereby significant female offsprings can be produced in mammals.

Another objective is to provide a method whereby the female population of livestock can be increased, to make cross-breeding programs with livestock of exotic breeds a tremendous success.

SUMMARY OF THE INVENTION

Accordingly, the invention provides an in vivo method whereby female offsprings can be produced in mammals, especially the bovine species, said method comprising the step of administering a therapeutically effective amount of dilute acetic acid, or its pharmaceutically acceptable derivatives to female mammals just after insemination.

DETAILED DESCRIPTION OF THE INVENTION

The present invention in its broadest aspect relates to a method for preferential production of female offsprings in mammals. The method of the invention is specifically applicable to members of the bovine family such as cows and buffaloes and other animals such as horses, sheep, dogs, goats, etc. It is the Applicant's finding that administration of dilute acetic acid, or its derivatives, (hereinafter as "the material" for sake of brevity) to a mammal, within about 30 minutes after insemination will lead to preferential production of female offsprings. In fact, it is the Applicant's experience that the offspring produced after such administration is generally female.

The method of the invention comprises the steps of insemination, artificial or natural of the female animal and administration of a therapeutically effective amount of the material, comprising essentially of a combination of acetic acid, its derivatives to the animal immediately after insemination. Thereafter, the animal is allowed to eat and resume its usual activities in its natural surroundings and environment.

By "therapeutically effective amount", the applicants imply an amount that will enable production of female offsprings. Again, the dosage or the amount of material to be administered will vary from animal to animal and can be readily determined by a person skilled in the art on the basis of body weight of the subject to which the material is to be administered. For the instance, in case of cows and buffaloes, the amount may be about 150 to 800 ml of the said material. Preferably, 250 to 400 ml of the material may be administered to the animal. In short, the amount administered should be such that it is not lethal to the animal.

It is the Applicant's finding that the material that causes production of female offsprings in mammals is a substance essentially comprising acetyl radical. Typical examples of such material are vinegar, dilute acetic acid, sodium acetate and the natural or synthetic derivatives thereof. The material may be obtained from natural sources or derived by synthetic methods.

The preferred material is vinegar. The essence of the invention lies in the use of a material rich in or essentially comprising acetic acid for administration to a mammal. The material known to be rich in acetic acid or vinegar as readily available. While the use of other such material falls within the scope of the invention. the applicants recommend the use of vinegar prepared by prolonged fermentation. The natural sources of vinegar are crushed beet juice, sugar cane juice, molasses etc. Such juices are subjected to extended periods of fermentation such as 2-8 months depending upon the season of the year. The fermentation may be preferably carried out in any earthenware under optimum environments. In a preferred embodiment, fermenting agents such as vinegar made previously by the same process or any other such fermenting agent may be added to the broth. However, with the application of modem technology, this preparation of vinegar can be effected within a short period of time, i.e. within 10 to 20 days or so, depending upon the quality of fermenting agents and physical and chemical environments maintained. The material may be decanted at regular intervals to avoid contamination and growth of unwanted organisms. The material produced at the end of such a process is essentially rich in acetic acid, and also contains traces of acetaldehyde, acetic anhydride and ethanol.

The materials that can be used for administration to the animal include dilute acetic acid, sodium or potassium acetate in acidic pH, both solutions preferably kept at a pH of about 3, the natural or synthetic derivatives thereof.

The insemination of the mammal may be effected naturally or by adoption of artificial methods as known in the art. In an embodiment, this material is administered to the animal as early as possible after insemination. The step of administration of the material to the animal may even precede the process of insemination as an alternate embodiment. In case of animals where repeated insemination occurs, such as in dogs, care is taken to ensure that the insemination is restricted to once only. It must also be ensured that the insemination is not subjected to prolonged or extended periods of time so that the peak levels for maximum effects of the material during the process of fertilization are realized.

The time period for the administration of the material to the animal is quite critical. The period may of course vary from one animal to the other, but the general thumb rule is administration of the material within 30 minutes after insemination. The reason is that the material must be administered to the animal before zygote formation. In any case, the material should be administered at least within one hour after insemination. If the material is to be administered before insemination, then it may be administered 1 or 3 hours before insemination.

After administering the material as a single dose, the fetus develops normally and the animal goes through, completes pregnancy and gives birth to totally normal and viable female offspring/s. It is found that the offsprings produced according to the method of the invention lead a normal life. Also these offsprings when mated with normal males, produce viable offsprings. The applicants have observed that administration of the material to the animal does not evoke any adverse reactions or side-effects like fever, skin reactions, behavioral changes etc. Hence the material of the invention can be readily and safely administered to the animals.

The route of administration of the material primarily depends on the subject. Hence, if the subject is bovine species, then oral route may be adopted. Familiar methods of oral administration routes include sublingual, nasal, buccal. Other routes of administration, such as cutaneous, subcutaneous, parenteral, vaginal, intra-urethral, anal routes, etc. may also be adopted.

The material may be administered as such or may be formulated in various physical forms such as solution, syrup, elixir, mixture, emulsion, suspension, tablet, capsule, pessary, suppository, aerosol or a parental preparation, etc. The dosage form may accordingly be varied. As such, there is no intention to limit the scope of the invention to any particular physical form. In accordance with the practice of the invention, pharmaceutical compositions containing the material as the primary active ingredient may be prepared. These compositions may be prepared according to any method known in the art for the manufacture of pharmaceutical compositions. Such compositions, if intended for oral use may contain one or more agents selected from the group consisting of sweetening agents, flavoring agents, coloring agents and preserving agents in order to provide pharmaceutically elegant and palatable preparations. Tablets are prepared containing the active ingredient i.e. the material, in admixture with non-toxic pharmaceutically acceptable excipients. Such excipients may be for example inert diluents, such as calcium carbonate, sodium carbonate, lactose, calcium phosphate or sodium phosphate; granulating and disintegrating agents, for example, corn starch, or alginic acid; binding agents, such as starch, gelatin or acacia, and lubricating agents like magnesium stearate, stearic acid or talc. The tablets may be uncoated or they may be coated by known techniques.

Compositions for oral use may also be presented as hard gelatin capsules wherein the active ingredient i.e. the material is mixed with an inert solid diluent, for example, calcium carbonate, calcium phosphate or kaolin, or as soft gelatin capsules wherein the active ingredient i.e. the material is mixed with water or an oil medium, for example peanut oil, liquid paraffin or olive oil.

The compositions may also be formulated as suppositories or pessary which can be prepared by mixing the material with suitable nonirritating excipients or carriers such as cocoa butter, polyethyleneglycol or a suppository wax, which are solid at ordinary temperatures but liquid at body temperature and therefore, melt in the rectum or vaginal cavity and release the active ingredient i.e. the material. In other words, all sorts of compositions that do not affect the efficacy of the material and are capable of keeping the active ingredient i.e. the material in effective contact with the uterine tissues are envisaged and envisaged within the scope of this invention.

The exact mechanism by which the material i.e. vinegar, dilute acetic acid and their natural or synthetic, derivatives act is not clear. However, it can be postulated that these materials can furnish an acetyl radical by certain biochemical interactions in the living system to participate in the Kreb's-cycle via the route of Acetyl-Co-Enzyme A. But even then the exact mechanism by which a change in normal metabolic pathway of the living system like Kreb's-cycle causes sex of the offspring to be determined is not clear. And it may also happen that above material does not interfere in normal metabolic pathways of the living systems but acts as a sex determinant by some other mechanism or biochemical pathway, known or unknown, to present day available scientific knowledge and data. Or, it may be that as certain reptiles and ratites do not have an organised sex chromatin and as they are phylogenic ancestors and relatives of mammals which are much evolved chordates and as a prominent principle in evolution states that progeny repeats phyllogeny; it may not be ruled out that under certain circumstances and stages of fertilization or zygotic or embryonic development, a given chromosome, say X-chromosome or a chromatin pattern, say XX may change into the other type, i.e. Y-chromosome or XY chromatin pattern and vice versa in some sort of imitation to the phenomenon of birth reversal found in certain reptiles and ratites.

The foregoing description of the invention is considered illustrative of some of the preferred embodiments of the invention. Various modifications and changes that can be readily made by a person skilled in the art, are considered to be encompassed within the scope of the present invention. Accordingly, the embodiments illustrated above and the following examples do not limit the scope of the invention to the exact features as herein described. Suitable modifications and equivalents may be resorted to, within the scope of the invention.

EXAMPLE 1

Preparation of Material 20 liters of sugarcane juice was obtained from crushed sugarcane. This juice was left in an earthen pot in the open for fermentation for a period of 6 months. A fermenting agent such as vinegar prepared previously by the same process was added on day 1 and day 10 to the juice in the earthen pot. The amount added was about 250 ml. The temperature prevalent during period was in the range of 25 to 35° C. The juice in the earthen pot was periodically monitored and decanted to ensure that contaminants and unwanted organisms do not infect it. At the end of six months, 4 to 5 liters of liquid was found in the earthen pot. This liquid was tested for its contents. This liquid contained the following:

| | |
|---|---|
| Dilute Acetic acid | 8 to 16% |
| Acetaldehyde | Traces |
| Acetic anhydride | Traces |
| Ethyl Alcohol | 4 to 9% |
| Rest water | to qs |

EXAMPLE 2

The study was conducted as under:

(1) Study on animals (cows and buffaloes) and on control groups using vinegar only.

(2) Study on animals (cows and buffaloes) with no control group using vinegar, acetic acid and sodium acetate.

(3) Study on other animals using vinegar only.

The first study was conducted in a population primarily comprising cows and buffaloes. The study had a total of 38 animals (26 buffaloes and 12 cows). Equal number of animals were used in the standard/control group for comparison. The animals were in the study group were allowed to undergo one insemination. Thereafter, i.e. within 35-50 minutes, the material prepared according to the process described in Example 1 was administered to the animals in the study group. The animals in the control/standard group were not subject to administration of any material. Mating or insemination was not controlled. All the animals were allowed to move freely in their usual environment and were kept on normal diet. Their behavior and temperature/temperament especially of the study group. was monitored. It was found to be normal. No skin reaction, rashes, etc. were detected. No unnatural behavior was observed in any of the animals. All animals that conceived in the study and the control group proceeded to pregnancy. Upon completion of pregnancy, it was noted that out of 38 animals in the study group, 30 animals delivered female calves. During this period, it was also noted that 7 did not conceive and one reported mis-carriage. In the control group where no vinegar was administered, out of 38 animals (i.e. 26 buffaloes and 12 cows), 5 did not conceive and 1 reported miscarriage. The remaining 32 animals delivered 16 males (46.87%) and 17 (53.13%) female offsprings. The results are depicted in Table 1. It is to be noted that the cases of miscarriage and non-conception are not abnormal as it is a general phenomenon in these animals.

TABLE 1

Effects of vinegar on study and control groups of animals

| Type of Animals | No. of Animals | No. of miscarriages | Animals not conceived | OFFSPRING Females | OFFSPRING Males |
|---|---|---|---|---|---|
| | STUDY | | | | |
| Buffaloes | 26 | 1 | 5 | 20 | Nil |
| Cows | 12 | Nil | 2 | 10 | Nil |
| | STANDARD | | | | |
| Buffaloes | 26 | 1 | 3 | 12 | 10 |
| Cows | 12 | Nil | 2 | 5 | 5 |

EXAMPLE 3

A similar study, as described in Example 2, was carried out on animals such as cows and buffaloes using study groups. These animals were administered vinegar, dilute acetic acid, and sodium acetate solution in acidic pH separately. The results of this study are described herein below and shown in Table 2.

A. Study using vinegar only: The study was carried on 21 animals (14 buffaloes and 7 cows) out of which 4 did not conceive and 1 reported miscarriage and the remaining 16 delivered 16 (100%) female offsprings.

B. Study using Acetic acid only: The study was conducted on 22 animals (14 buffaloes and 8 cows) out of which 5 did not conceive; no animals reported miscarriage and remaining the 17 animals delivered 17 (100%) female offsprings.

C. Study using sodium acetate solution in Acidic pH: The study was conducted on 15 animals (10 buffaloes and 5 cows) out of which there were 3 cases of no conception and remaining 12 animals delivered 12 (100%) female offsprings.

TABLE 2

Study on animals with no control group using vinegar acetic acid dilute and sodium acetate solution in acidic -pH

| Type of preparation used | Type of Animals | No. of Animals | No. of Miscarriages | Animals not conceived | OFFSPRING Females | OFFSPRING Males |
|---|---|---|---|---|---|---|
| Vinegar | Buffaloes | 14 | 1 | 3 | 10 | Nil |
| | Cows | 7 | Nil | 1 | 6 | Nil |
| Acetic Acid dilute | Buffaloes | 14 | Nil | 3 | 11 | Nil |
| | Cows | 8 | Nil | 2 | 6 | Nil |
| Sodium Acetate Acidified | Buffaloes | 10 | Nil | 2 | 8 | Nil |
| | Cows | 5 | Nil | 1 | 4 | Nil |

EXAMPLE 4

In order to ascertain the efficacy of vinegar/acetic acid on other mammals, a study, as discussed in Examples 2 and 3 was conducted on sheep. The study had 20 sheep in the study group and 20 animals in the control group. At the end of the study, it was found that the sheep in the study group that were administered vinegar (50-60 ml/dose) gave birth to 28 female offsprings. No male offspring was produced. 5 animals did not conceive and one animal reported miscarriage. The animals in the control group, on the other hand, produced male and female offsprings. The results are shown in Table 3 herein below:

TABLE 3

Study on sheep using vinegar

| | No. of animals | Animals not conceived | No. of miscarriages | OFFSPRING Males | OFFSPRING Females |
|---|---|---|---|---|---|
| Study | 20 | 5 | 1 | Nil | 28 |
| Control | 20 | 3 | 1 | 8 | 16 |

EXAMPLE 5

In order to ascertain the efficacy of vinegar/acetic acid on mammals such as horses, a study, as discussed in Examples 2 and 3 was conducted. The dosage of administration of vinegar was 250-400 ml. At the end of the study wherein 26 horses were employed, it was found that 17 female offsprings were produced. No male offspring was produced. 7 animals did not conceive and two animals reported miscarriage. The results are shown in Table 4 herein below:

TABLE 4

Study on horses using vinegar

| No. of animals | Animals not conceived | No. of miscarriages | OFFSPRING Males | OFFSPRING Females |
|---|---|---|---|---|
| 26 | 7 | 2 | Nil | 17 |

EXAMPLE 6

In order to ascertain the efficacy of vinegar/acetic acid on goats, a study, as discussed in Examples 2 and 3 was conducted. The study had 19 goats. The animals were given 50-60 ml of vinegar after the insemination. At the end, of the study wherein 19 goats were employed, it was found that 26 female offsprings were produced. No male offspring was produced by the goats. 6 animals did not conceive and no cases of miscarriage were reported. The results are shown in Table 5, herein below:

TABLE 5

Study on goats using vinegar

| No. of animals | Animals not conceived | No. of miscarriages | OFFSPRING Males | OFFSPRING Females |
|---|---|---|---|---|
| 19 | 6 | Nil | Nil | 26 |

EXAMPLE 7

Yet another study on pigs was conducted following the method discussed in Example 2 and 3. The pigs were given 150 to 250 ml of vinegar. At the end of the study wherein 7 pigs were employed, it was found that 47 female offsprings were produced. No male offspring was produced. 2 animals did not conceive and no cases of miscarriage were reported. The results are shown in Table 6, herein below:

TABLE 6

Study on pigs using vinegar only

| No. of animals | Animals not conceived | No. of miscarriages | OFFSPRING Males | OFFSPRING Females |
|---|---|---|---|---|
| 7 | 2 | Nil | Nil | 47 |

EXAMPLE 8

A study on dogs based on the method described in Examples 2 and 3 was conducted on dogs. Vinegar was given to all the animals @45-55 ml. At the end of the study wherein 9 dogs were employed, it was found that 29 female offsprings were produced. No male offspring was produced. 2 animals did not conceive and no cases of miscarriage were reported. The results are shown in Table 7, herein below:

TABLE 7

Study on dogs using vinegar

| No. of animals | Animals not conceived | No. of miscarriages | OFFSPRING Males | OFFSPRING Females |
|---|---|---|---|---|
| 9 | 2 | Nil | Nil | 29 |

EXAMPLE 9

7 persons who had no female children in their family, came forth as volunteers. They were informed about the study conducted in animals and the efficacy of the material. The method, mode and dosage of administration (65-80 ml) was also discussed. The volunteers co-operated and at the end of the study, 7 girl children were born. No males or cases of miscarriage were reported. The results are shown in Table 8, herein below:

TABLE 8

Study on humans using vinegar

| No. of human subjects | No. of miscarriages | OFFSPRING Males | OFFSPRING Females |
|---|---|---|---|
| 7 | Nil | Nil | 7 |

The invention claimed is:

1. An in vivo method for the preferential production of female offspring in a bovine, said method comprising the step of orally administering a material comprising a therapeutically effective amount of acetic acid and/or its pharmaceutically acceptable derivatives to the bovine in a time period defined as 3 hours before insemination of the bovine to 1 hour after insemination of the bovine, provided that the material is administered to the bovine before zygote formation.

2. The method as claimed in claim 1 wherein the material comprises vinegar, sodium acetate and/or their natural or synthetic derivatives.

3. The method as claimed in claim 1 wherein the material comprises 8-16% dilute acetic acid.

4. The method as claimed in claim 1 wherein the amount of the material administered to the bovine is in the range of 150 ml to 800 ml.

5. The method as claimed in claim 1 wherein the amount of the material administered to the bovine is in the range of 250 ml to 400 ml.

6. The method as claimed in claim 1 wherein the material is administered after insemination but before zygote formation.

7. The method as claimed in claim 1 wherein the material is formulated in a physical form selected from the group consisting of a solution, a syrup, an elixir, a mixture, an emulsion, a suspension, a tablet, and a capsule.

8. The method as claimed in claim 1 wherein the material is administered within three hours before zygote formation.

9. The method as claimed in claim 1 wherein the material is administered to the bovine within 30 minutes after insemination of the bovine.

10. The method as claimed in claim 1 wherein the material is administered to the bovine one hour before insemination of the bovine.

* * * * *